United States Patent [19]
Huval et al.

[11] Patent Number: 6,083,497
[45] Date of Patent: Jul. 4, 2000

[54] METHOD FOR TREATING HYPERCHOLESTEROLEMIA WITH UNSUBSTITUTED POLYDIALLYLAMINE POLYMERS

[75] Inventors: Chad Cori Huval, Somerville; Stephen Randall Holmes-Farley, Arlington; John S. Petersen; Pradeep K. Dhal, both of Acton, all of Mass.

[73] Assignee: GelTex Pharmaceuticals, Inc., Waltham, Mass.

[21] Appl. No.: 08/964,536

[22] Filed: Nov. 5, 1997

[51] Int. Cl.[7] ............................. A61K 31/787; A61P 7/02
[52] U.S. Cl. ......................................... 424/78.35; 514/824
[58] Field of Search ............................. 424/400, 78.35; 514/824

[56] References Cited

U.S. PATENT DOCUMENTS

| | | | |
|---|---|---|---|
| 2,926,161 | 2/1960 | Butler et al. | 260/89.7 |
| 3,288,770 | 11/1966 | Butler | 260/88.3 |
| 3,700,623 | 10/1972 | Keim | 260/80.3 R |
| 3,833,531 | 9/1974 | Keim | 260/29.6 CM |
| 3,840,504 | 10/1974 | Keim | 260/79.3 A |
| 3,966,694 | 6/1976 | Espy et al. | 526/11.2 |
| 3,990,958 | 11/1976 | Sasse | 204/159.22 |
| 4,121,986 | 10/1978 | Battaerd | 204/159.22 |
| 4,298,715 | 11/1981 | Van Eenam | 525/340 |
| 4,452,957 | 6/1984 | Neigel | 526/71 |
| 4,759,923 | 7/1988 | Buntin et al. | 424/440 |
| 4,812,540 | 3/1989 | Kageno et al. | 526/218.1 |
| 5,200,482 | 4/1993 | Gartner | 526/295 |
| 5,428,112 | 6/1995 | Ahlers et al. | 525/326.7 |
| 5,430,110 | 7/1995 | Ahlers et al. | 525/328.2 |
| 5,607,669 | 3/1997 | Mandeville, III et al. | 424/78.12 |
| 5,618,530 | 4/1997 | Mandeville, III et al. | . |
| 5,624,963 | 4/1997 | Mandeville, III et al. | . |
| 5,679,717 | 10/1997 | Mandeville, III et al. | 514/742 |
| 5,693,675 | 12/1997 | Mandeville, III et al. | 514/742 |
| 5,703,188 | 12/1997 | Mandeville, III et al. | 526/290 |

FOREIGN PATENT DOCUMENTS

| | | |
|---|---|---|
| 0 375 350 A2 | 6/1990 | European Pat. Off. . |
| 0 580 078 A1 | 1/1994 | European Pat. Off. . |
| 0 580 079 A1 | 1/1994 | European Pat. Off. . |
| 0 665 245 A1 | 8/1995 | European Pat. Off. . |
| 2 090 605 | 7/1982 | United Kingdom . |
| WO 98/29107 | 7/1998 | WIPO . |

OTHER PUBLICATIONS

McCarthy, Peter A., "New Approaches to Atherosclerosis: An Overview." *Medicinal Research Reviews*, 13(2):139–159 (1993).

Heming, Arthur E. and Thomas L. Flanagan, "Considerations in the Selection of Cation Exchange Resins for Therapeutic Use." In *Annals of the New York Academy of Sciences*, 57:239–251 (1954).

Harada, Susumu and Kunio Arai, "The Cyclo–copolymerization of Diallyl Compounds and Sulfur Dioxide, II. Diallyldimethylammonium Chloride and Sulfur Dioxide," *Die Makromolekulare Chemie* 107:64–77 (1967).

Negi, Youji et al., "Cyclopolymerization of Diallylamine Derivatives in Dimethyl Sulfoxide," *Journal of Polymer Science: Part A–1*, 5:1951–1965 (1967).

Kuron, G.W. et al., "The Bile Acid Binding and Hypocholesterolemic Action of Two Water–Soluble Polymers," *Atherosclerosis* 37:353–360 (1980).

Hodgkin, J.H. et al., "Use of $^{13}$C–NMR in the Study of Reactions on Crosslinked Resins," *Journal of Polymer Science* 19(5):1239–1249 (1981).

United States Serial No. 08/777,408, filed on Dec. 30, 1996, "Poly (diallylamine)—Based Bile Acid Sequestrant" by Stephen Randall Holmes–Farley, Pradeep K. Dhal and John S. Petersen.

*Primary Examiner*—Edward J. Webman
*Attorney, Agent, or Firm*—Hamilton, Brook, Smith & Reynolds, P.C.

[57] ABSTRACT

A method for removing bile salts from a patient that includes administering to the patient a therapeutically effective amount of a non-absorbable polydiallylamine polymers.

12 Claims, No Drawings

METHOD FOR TREATING HYPERCHOLESTEROLEMIA WITH UNSUBSTITUTED POLYDIALLYLAMINE POLYMERS

BACKGROUND OF THE INVENTION

Reabsorption of bile acids from the intestine conserves lipoprotein cholesterol in the bloodstream. Conversely, blood cholesterol levels can be diminished by reducing reabsorption of bile acids.

One method of reducing the amount of bile acids that are reabsorbed and, thus, reducing serum cholesterol is the oral administration of compounds that sequester the bile acids and cannot themselves be absorbed. The sequestered bile acids are excreted.

Compounds which have been suggested for bile acid sequestration include various ion exchange polymers. One such polymer is cholestyramine, a copolymer of divinylbenzene and trimethylammoniummethyl styrene. It has been long recognized that this polymer is unpalatable, gritty, and constipating. More recently, various polymers have been suggested which are characterized by hydrophobic substituents and quaternary ammonium radicals substituted upon an amine polymer backbone (Ahlers, et al. U.S. Pat. Nos. 5,428,112 and 5,430,110 and McTaggert, et al., U.S. Pat. No. 5,462,730, which are incorporated herein by reference). In some cases, these polymers have ha d disappointing efficacy and require complex processes for their manufacture.

Thus, there is still a need to discover superior bile acid sequestrants.

SUMMARY OF THE INVENTION

The invention relates to the unexpected discovery that a new class of ion exchange resins have improved bile salt sequestration properties. The polymers, or resins, employed in the invention comprise non-absorbable, and optionally cross-linked polydiallylamines. The polydiallylamines of the invention are characterized by one or more monomeric units of the formulae:

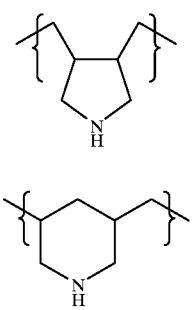

(I)

(II)

or a combination thereof and salts thereof. The polymer can be characterized by the substantial absence of one or more alkylated amine monomers and/or the substantial absence of one or more trialkylammonium alkyl groups. In preferred embodiments, the polymer is crosslinked by means of a multifunctional crosslinking agent. The polymer can also be characterized as being linear or branched.

The invention provides an effective treatment for removing bile salts from a patient (and thereby reducing the patient's cholesterol level). The invention also provides for the use of the polymers described herein in therapy or for the manufacture of a medicament for the treatment of hypercholesterolemia or for bile acid sequestration.

Other features and advantages will be apparent from the following description of the preferred embodiments thereof and from the claims.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principal features of the invention can be employed in various embodiments without departing from the scope of the present invention.

The invention provides a method for removing bile acids from a patient comprising administering to the patient a therapeutically effective amount of a polymer characterized by a diallylamine monomer, or repeat unit.

As used herein, the term "therapeutically effective amount" refers to an amount which is sufficient to remove a significant quantity of bile acids from the patient and, thus, to lower the serum cholesterol level of the patient. The patient can be an animal, for example, a mammal, or a human.

As described above, the polymers employed in the invention comprise non-absorbable, optionally cross-linked polydiallylamines characterized by the formula above. Importantly, the polymers can be characterized by the substantial absence of substituted or unsubstituted alkyl substituents on the amino group of the monomer, such as obtained in the alkylation of an amine polymer. That is, the polymer can be characterized in that the polymer is substantially free of alkylated amine monomers.

The polymer can be a homopolymer or a copolymer. Where copolymers are manufactured with a diallylamine monomer, the comonomers are preferably inert, non-toxic and/or possess bile acid sequestration properties. Suitable examples of additional comonomers include substituted and unsubstituted acrylate, substituted and unsubstituted acrylamide, substituted and unsubstituted methacrylate, substituted and unsubstituted methacrylamide, allylamine, triallylamine, allyl alcohol, substituted and unsubstituted vinyl amine and substituted and unsubstituted vinyl alcohol. In one embodiment, the additional monomer is sulfur dioxide. Preferably, the monomers are aliphatic. Most preferably, the polymer is a homopolymer, i.e. a homopolydiallylamine.

Preferably, the polymer is rendered water-insoluble by branching and/or crosslinking. The cross-linking agent can be characterized by functional groups which react with the amino group of the monomer. Alternatively, the crosslinking group can be characterized by two or more vinyl groups which undergo free radical polymerization with the amine monomer. Suitable multifunctional co-monomers include triallylamine, tetraallyleammonium salts, bis(diallylamine)s (such as alkylene bis(diallylamine)s), diacrylates, triacrylates and tetraacrylates, dimethacrylates, diacrylamides, diallylacrylamide and di(methacrylamides). Specific examples include ethylene bis(diallylamine), hexamethylene bis(diallylamine), ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The polymer can alternatively be crosslinked by bridging units which link amino groups on adjacent polymer strands. Suitable bridging units include straight chain or branched, substituted or unsubstituted alkylene groups, diacylalkylene groups, diacylarene groups and alkylene bis(carbamoyl) groups. Examples of suitable bridging units include —($CH_2$)$_n$—, wherein n is an integer from about 2 to about 20; —$CH_2$—CH(OH)—$CH_2$—; —C(O)$CH_2CH_2$C(O)—; —$CH_2$—CH(OH)—O—($CH_2$)$_n$—O—CH(OH)—$CH_2$—, wherein n is 2 to about 4; —C(O)—($C_6H_2$(COOH)$_2$)—C(O)— and —C(O)NH($CH_2$)$_p$NHC(O)—, wherein p is an integer from about 2 to about 20.

Examples of suitable crosslinking agents include acryloyl chloride, epichlorohydrin, butanedioldiglycidyl ether, ethanedioldiglycidyl ether, and dimethyl succinate.

A preferred crosslinking agent is epichlorohydrin because of its high availability and low cost. Epichlorohydrin is also advantageous because of it's low molecular weight and hydrophilic nature, increasing the water-swellability of the polyamine.

The level of crosslinking makes the polymers insoluble and substantially resistant to absorption and degradation, thereby limiting the activity of the polymer to the gastrointestinal tract. Thus, the compositions are non-systemic in their activity and will lead to reduced side-effects in the patient. Typically, the cross-linking agent is present in an amount from about 0.5–50% (more preferably about 0.5–30% and most preferably about 2–20%) by weight, based upon total weight of monomer plus crosslinking agent.

When used in a non-crosslinked form, polymers of use in the present method are, preferably, of a molecular weight which enables them to reach and remain in the gastrointestinal tract for a sufficient period of time to bind a significant amount of one or more bile acids. These polymers should, thus, be of sufficiently high molecular weight to resist, partially or completely, absorption from the gastrointestinal tract into other regions of the body. The resulting polymer/bile salt complex should then be excreted from the body. Suitable linar (non-crosslinked) polymers have molecular weights which range from about 2,000 Daltons to about 500,000 Daltons, preferably from about 5,000 Daltons to about 150,000 Daltons. Crosslinked polymers, however, are not generally characterized by molecular weight. The crosslinked polymers discussed herein should be sufficiently crosslinked to resist adsorption from the gastrointestinal tract.

As described above the polymer can be administered in the form of a salt, or as a partial salt. By "salt" it is meant that the nitrogen groups in all or some of the repeat units are protonated to create a positively charged nitrogen atom associated with a negatively charged counterion.

The anionic counterions can be selected to minimize adverse effects on the patient, as is more particularly described below. Examples of suitable counterions include $Cl^-$, $Br^-$, $CH_3OSO_3^-$, $HSO_4^-$, $SO_4^{2-}$, nitrate, $HCO_3^-$, $CO_3^{2-}$-acetate, lactate, phosphate, hydrophosphate, methanesulfonate, fumarate, malate, pyruvate, malonate, benzoate, glucuronate, oxalate, acetylglycinate, succinate, propionate, butyrate, ascorbate, citrate, tartrate, maleate, folate, an amino acid derivative, a nucleotide, a lipid, or a phospholipid. The counterions can be the same as, or different from, each other. For example, the reaction product can contain two different types of counterions.

The polymers according to the invention can be administered orally to a patient in a dosage of about 1 mg/kg/day to about 10 g/kg/day, preferably between about 1 mg/kg/day to about 200 mg/kg/day; the particular dosage will depend on the individual patient (e.g., the patient's weight and the extent of bile salt removal required). The polymer can be administrated either in hydrated or dehydrated form, and can be flavored or added to a food or drink, if desired, to enhance patient acceptability. Additional ingredients such as other bile acid sequestrants, drugs for treating hypercholesterolemia, atherosclerosis or other related indications, or inert ingredients, such as artificial coloring agents can be added as well.

Examples of suitable forms for administration include pills, tablets, capsules, and powders (e.g., for sprinkling on food). The pill, tablet, capsule, or powder can be coated with a substance capable of protecting the composition from disintegration in the esophagus but will allow disintegration of the composition in the stomach and mixing with food to pass into the patient's small intestine. The polymer can be administered alone or in combination with a pharmaceutically acceptable carrier, diluent or excipient substance, such as a solid, liquid or semi-solid material. Examples of suitable carriers, diluents and excipients include lactose, dextrose, sucrose, sorbitol, mannitol, starches, gum acacia, alginates, tragacanth, gelatin, calcium silicate, cellulose e.g., magnesium carbonate or a phospholipid with which the polymer can form a micelle.

Polymers of use in the present method can be prepared using techniques known in the art of polymer synthesis (see for example, Shalaby et al., ed., Water-Soluble Polymers, American Chemical Society, Washington D.C. (1991)). For example, the appropriate monomer(s) can be polymerized by methods known in the art, for example, via a free radical addition process. In this case the polymerization mixture includes a free-radical initiator, such as a free radical initiator selected from among those which are well known in the art of polymer chemistry. Suitable free-radical initiators include azobis(isobutyronitrile), azobis(4-cyanovaleric acid), azobis(amidinopropane) dihydrochloride, potassium persulfate, ammonium persulfate and potassium hydrogen persulfate. The free radical initiator is preferably present in the reaction mixture in an amount ranging from about 0.1 mole percent to about 5 mole percent relative to the monomer.

The polymer can be crosslinked, for example, by including a multifunctional co-monomer as the crosslinking agent in the reaction mixture. A multifunctional co-monomer can be incorporated into two or more growing polymer chains, thereby crosslinking the chains. Suitable multifunctional co-monomers include those discussed above.

The polymers can also be crosslinked subsequent to polymerization by reacting the polymer with one or more crosslinking agents having two or more functional groups, such as electrophilic groups, which react with amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl-X, epoxide, and alkyl-X, wherein X is a suitable leaving group, such as a halo, tosyl, mesyl, acyl or glycidyl group. Examples of such compounds include epichlorohydrin, succinyl dichloride, butanedioldiglycidyl ether, ethanedioldiglycidyl ether, pyromellitic dianhydride and dihaloalkanes. The crosslinking agent cn also be an α, ω-alkylene diisocyanate, for example OCN($CH_2$)$_p$NCO, wherein p is an integer from about 2 to about 20.

The polymer can also be crosslinked using a crosslinking agent which incorporates one functional group which incorporates into the polymerizing chain and a second functional group which can react with amine groups in a second polymer chain. Examples include glycidyl methacrylate, glycidyl acrylate, acryloyl chloride, methacryloyl chloride, 3-bromopropylacrylate, 3-bromopropylmethyldiallylammonium chloride, and 3-chloropropyldiallylamine.

The invention will now be described more specifically by the examples.

EXAMPLE 1

Preparation of Poly(diallylammonium chloride)

Concentrated hydrochloric acid (507.0 g; 37%) was charged to a 5L, 3-neck round bottomed flask and agitated with a mechanical stirrer. The flask was cooled to <5° C. with an ice bath. Diallylamine (635.0 ml) was added dropwise to the stirring hydrochloric acid over a three hour period using an addition funnel capped with a pierced rubber septum. The stirring solution temperature was maintained at <10° C. After the addition was completed, the ice bath was removed and the mixture was allowed to warm to room temperature. Concentrated hydrochloric acid (7.3 g) was added to the solution. Water (368.7 g) was added to the solution and it was allowed to sit overnight.

The stirring solution was purged with nitrogen gas for 30 minutes at room temperature. 2,2'-Azobis[2-amidinopropane]dihydrochloride (6.87 g) was added as 34.4 g of a 20% aqueous solution. The solution was heated to 60°–80° C. for six and one-half hours. 2,2'-Azobis[2-amidinopropane] dihydrochloride (6.87 g) was added as a 20% aqueous solution. The solution was stirred and heated overnight (16 hours).

2,2'-Azobis[2-amidinopropane]dihydrochloride (6.87 g) was added as a 20% aqueous solution. The solution was stirred and heated for another 16 hours, then cooled to room temperature.

Sodium hydroxide (53.8 g) was dissolved in $H_2O$ (2156 mL). The polydiallylamine-HCl solution was then added to the sodium hydroxide solution and agitated with a mechanical stirrer until dissolved. Concentrated hydrochloric acid (49.8 g; 37%) was added.

EXAMPLE 2

Synthesis of Polydiallylamine

A solution of 39.3 g of an aqueous solution (68 wt %) of diallylammonium hydrochloride, 5.3 g of an aqueous solution (73 wt %)of triallylamine hydrochloride and 0.9 g of 2,2'-azobis(2-amidinopropane)dihydrochloride was bubbled with a slow stream of nitrogen for 30 minutes. While stirring, this reaction mixture was added to a solution of 7 g of polyvinylacetate in 300 mL of toluene. The resulting mixture was stirred at room temperature for 45 minutes under nitrogen atmosphere. While stirring, the temperature of the reaction mixture was raised to 60 C and was held at this temperature for 24 hours. The reaction mixture was allowed to cool to room temperature and the polymer particles were collected by filtration. While in the funnel, the filtered particles were successively washed with 300 mL of toluene and 500 mL of methanol. The polymer particles were suspended in 500 mL of methanol, stirred for 50 minutes, and filtered. Subsequently, the particles were suspended in 400 mL of deionized water, stirred for 30 minutes and filtered. The filtered particles were dried at 60 C for 24 hr to yield 15 g of the polymer.

EXAMPLE 3

Cross-linked Polydiallylamine

The polymer solution of Example 1 was crosslinked at 30 mole % as follows:

Epichlorohydrin (31.61 mL) was added to 900.0 g of the neutralized polymer solution in a glass beaker, agitated with a magnetic stirrer and covered with polyvinyl film. The gel was allowed to cure for 22 hours. The solid gel was then ground using a Kitchen Aid grinder. The ground polymer was washed in a static bed manner using a large plastic Buchner funnel lined with filter paper. A second piece of filter paper, perforated with holes, was placed on top of the polymer cake to prevent disturbing the cake when adding wash water. Fresh deionized $H_2O$(14 L) was added to the top of the cake and drained under vacuum. The washed polymer was then transferred to glass drying trays and dried in a 60° C. forced air oven for several days. The final dry weight was 176.2 g.

EXAMPLE 4

Crosslinked Polydiallylamine

Using the same procedure as in Example 3, the neutralized polymer solution was crosslinked at 20 mole %. Epichlorohydrin (21.07 mL) was added to 900.0 g of the neutralized polymer solution. The final dry weight was 163.3 g.

EXAMPLE 5

Crosslinked Polydiallylamine

Using the same procedure as in Example 3, the neutralized polymer solution was crosslinked at 10 mole W %. Epichlorohydrin (10.54 mL) was added to 900.0 g of the neutralized polymer solution. The final dry weight was 164.2 g.

EXAMPLE 6

Crosslinked Polydiallylamine

Using the same procedure as in Example 3, the neutralized polymer solution was crosslinked at 4.5 mole %. Epichlorohydrin (4.74 mL) was added to 900.0 g of the neutralized polymer solution. The final dry weight was 176.2 g.

EXAMPLE 7

Copolymer of Diallylamine and Methylenebisacrylamide

A solution of diallylammoniuim chloride (73.53 g of 68% aqueous solution), methylenebisacrylamide (2.93 g, 0.019 mol), 2,2'-azobis(2-amidinopropane)dihydrochloride (V50) (0.5 g) and water (27 mL) was heated at 70° C. under a nitrogen atmosphere. Water (100 mL) was added after 15 minutes of reaction. An additional 0.5 g of V50 was added after 3 hours and again after 4 more hours. After keeping the reaction at 70 C for a total of 72 hr, it was cooled to room temperature. The resulting material was filtered and washed with 2 M NaCl (400 mL), and filtered and washed with water (2.5 L) and filtered again. The washed polymer was dried at

EXAMPLE 8

Copolymer of Diallylamine and Acrylamide

A solution of diallylammonium chloride (73.53 g of 68% aqueous solution), methylenebisacrylamide (2.93 g, 0.019 mol), 2,2'-azobis(2-amidinopropane) dihydrochloride (0.5 g) and water (27 mL) was heated at 70° C. under a nitrogen atmosphere for 3 days. Water (100 mL) was added after the first 15 minutes of reaction. 2,2'-Azobis(2-amidinopropane) dihydrochloride (0.5 g) was added after 3 hours and 7 hours. The resulting material was filtered and washed with 2 M NaCl (400 mL) and water (2.5 L). The washed polymer was dried at 60° C. in a forced-air oven to give 18.8 g of a solid.

EXAMPLE 9

Copolymer of Diallylamine, Acrylamide and Methylenebisacrylamide

A solution of diallylammonium chloride (14.7 g of 68% aqueous), acrylamide (5.33 g), methylenebisacrylamide (2.31 g), MeOH (50 mL), and 2,2'-azobis(2-amidinopropane)dihydrochloride (0.07 g of an 18.8% solution of water) was heated at 65° C. under a nitrogen atmosphere for 20 hours. The resulting material was suspended in methanol (500 mL), stirred for 15 minutes and filtered. This methanol wash was repeated twice more. The washed polymer was suspended in water (500 mL) and this mixture was acidified with concentrated HCl to pH 2.4. Filtration, and drying at 60° C. in a forced-air oven gave 9.8 g of a solid.

EXAMPLE 10

Copolymer of Diallylamine, a Functionalized Acrylic Ester and an Acrylic Ester Cross-linking Monomer A solution of diallylammonium chloride (14.7 g of 68% aqueous), 2-hydroxyethylmethacrylate (9.76 g), ethyleneglycol dimethacrylate (2.97 g), MeOH (25 mL), and 2,2'-azobis(2-amidinopropane) dihydrochloride (0.07 g of an 18.8% aqueous solution) was heated at 65° C. under a nitrogen atmosphere for 20 hours. The resulting material was suspended in methanol (500 mL), stirred for 15 minutes and filtered. The polymer was similarly washed three times with water (500 mL). This methanol wash and filtration were repeated twice more. The washed polymer was suspended in water (500 mL) and this mixture was acidified with concentrated HCl to pH 2.1. Filtration and drying at 60° C. in a forced-air oven gave 13.9 g of a solid.

EXAMPLE 11

Copolymer of Diallylamine, a Functionalized Acrylic Ester and an Acrylic Ester Cross-linking Monomer A solution of diallylammonium chloride (22.06 g of a 68% aqueous solution), tetrahydrofurfuryl methacrylate (18.72 g), ethyleneglycol dimethacrylate (4.36 g) and 2,2'-azobis(2-amidinopropane) dihydrochloride (2.03 g of an 18.8% aqueous solution) was heated at 65° C. under a nitrogen atmosphere for 24 hours. The resulting material was suspended in methanol (300 mL), stirred 15 minutes and filtered. This methanol wash and filtration was repeated twice more. The polymer was similarly washed three times with water (500 mL). The material was suspended in water (500 mL) and this mixture was acidified with concentrated HCl to pH 2.0. Filtration, and drying at 60° C. in a forced-air oven gave 19.9 g of a solid.

EXAMPLE 12

Copolymer of Diallylamine and Glycidylmethacrylate

A solution of diallylammoniium chloride (29.42 g of a 68% aqueous solution), glycidylmethacrylate (2.13 g), MeOH (25 mL), and 2,2'-azobis(2-amidinopropane) dihydrochloride (1.18 g of an 18.8% aqueous solution) was heated at 65° C. under a nitrogen atmosphere for 12 hours. After cooling to room temperature, methanol (25 mL) was added and the pH of the solution was adjusted to 10 with the addition of 50% aqueous NaOH, and allowed to stir at room temperature. The reaction solution turned to a solid mass after about 2 hours, and was allowed to stand for 22 hours. The resulting gel, was suspended in MeOH (300 mL), stirred and filtered. This methanol wash and filtration were repeated twice more. The polymer was then suspended in water (1 L). Concentrated HCl was added to this suspension until pH 2.0 and stirred 0.5 hours. Filtration and drying in a forced-air oven at 60° C. gave 6.0 g of a solid.

EXAMPLE 13

Copolymer of Allylamine, Diallylamine, Triallylamine and a Bis(diallylamino)alkylene Salt A solution of allylammonium chloride (25.0 g of a 60% aqueous solution), diallylammonium chloride (66.81 g of a 67% aqueous solution), triallylammonium chloride (40.87 g of a 68% aqueous solution), 1,6-bis (diallylmethylammoniium)hexane dibromide (5.0 g), and 2,2'-azobis(2-amidinopropane) dihydrochloride (4.28 g of a 20% aqueous solution), was heated at 55° C. under a nitrogen atmosphere for 18 hours and at 80° C. for 2 hours. After cooling to room temperature, the gel was suspended in MeOH (500 mL), stirred 15 minutes and filtered. This method was repeated. The polymer was suspended in water (1.0 L) and stirred at least 15 minutes and filtered. After drying in a 60° C. forced-air oven, 31.9 g of solid was isolated.

EXAMPLE 14

Copolymer of Allylamine and Diallylamine

A solution of allylammonium chloride (54.71 g of a 57% aqueous solution), diallylammonium chloride (132.96 g of a 67% aqueous solution), and 2,2'-azobis(2-amidinopropane) dihydrochloride (6.01 g of a 20% aqueous solution), was heated at 55° C. under a nitrogen atmosphere for 36 hours. Another portion of 2,2'-azobis(2-amidinopropane) dihydrochloride (6.01 g of a 20% aqueous solution) was added after the first 18 hours. After cooling to room temperature, the solution was added slowly to IPA (3 L), and the precipitate after decanting the IPA layer, was washed with IPA (3 L) and filtered. The precipitate was dried in a forced-air oven at 60° C. to afford 106.9 g of a solid.

EXAMPLE 15

Copolymer of Allylamine, Diallylamine and a Bis (diallylamino)alkylene

A solution of allylammonium chloride (27.36 g of a 57% aqueous solution), diallylammonium chloride (66.48 g of a 67% aqueous solution), 1,6-bis(diallylmethylammonium) hexane dibromide (10.0 g), and 2,2'-Azobis(2-amidinopropane) dihydrochloride (3.01 g of a 20% aqueous solution(, was heated at 55° C. under a nitrogen atmosphere for 36 hours. Another portion of 2,2'-Azobis(2-amidinopropane) dihydrochloride (3.01 g of a 20% aqueous solution) was added after the first 18 hours. A gel formed after about 24 hours of heating. After cooling to room temperature, this material was washed with MeOH (500 mL) and filtered three times, as described above. The polymer was then suspended and washed with water (2.5 L). After filtration, the wet material was dried in a forced-air oven at 60° C. to afford 24.8 g of a solid.

EXAMPLE 16

In Vivo Testing

Male Golden Syrian Hamsters were group housed in shoe box cages and acclimated for approximately 1 week in our animal facility. Animals were fed rodent chow (brown color) and water ad libitum. The hamsters were then transferred to metabolism cages and housed individually. Following a 24 hour fast (water ad libitum), animals were presented a casein-based purified diet (white color) with 10% fat added plus the drug to be evaluated. Fecal material was collected from 9 hours after the casein-based diet was presented for 39 additional hours. The white fecal pellets (drug-containing casein-based diet) were lyophilized and ground to a homogeneous powder. One gram of the ground fecal pellet was extracted in a solution consisting of methanol and 500 mM aqueous NaOH (4:1; v/v) at 100° C. and 1500 psi for 15 minutes. A 500 uL aliquot of the extract was evaporated and reconstituted in 1500 uL bovine calf serum:0.9% saline (1:1) and analyzed enzymatically, utilizing a test kit for bile acids (Sigma Chemical Co., St. Louis, Mo.) for bile acid concentration.

TABLE

| Polymer | Dose (% in feed) | Fecal Bile Acids ($\mu$mol/g) |
|---|---|---|
| None | None | 1.34 |
| Example 6 | .10 | 2.19 |
| Example 6 | .15 | 3.44 |
| Example 6 | .20 | 3.72 |
| Example 6 | .25 | 3.48 |
| Cholestyramine | 0.30 | 3.00 |
| Colestipol | 0.30 | 2.81 |

This example shows that crosslinked polydiallylamine is a highly potent bile acid sequestrant, with in vivo activity greater than current commercial products, Colestipol and Cholestyramine.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for removing bile salts from a patient comprising administering to said patient a therapeutically effective amount of a polydiallylamine polymer, said polymer characterized in that the polymer is free of alkylated amine monomers.

2. The method of claim 1 wherein said polymer is crosslinked by means of a multifunctional crosslinking agent, said agent being present in an amount from about 0.5–50% by weight, based upon the combined weight of monomer and crosslinking agent.

3. The method of claim 2 wherein said crosslinking agent is present in an amount from about 2.5–20% by weight, based upon the combined weight of monomer and crosslinking agent.

4. The method of claim 2 wherein said crosslinking agent comprises epichlorohydrin.

5. The method of claim 2 wherein said crosslinking agent is a bis(diallylammonium)dialkylene ion.

6. The method of claim 1 wherein the polymer is a homopolymer.

7. A method of claim 1 wherein the polymer is a copolymer.

8. A method of claim 7 wherein the copolymer comprises the monomers diallylamine, allylamine, and triallylamine.

9. A method of claim 7 wherein the copolymer comprises the monomers diallylamine and allylamine.

10. A method of removing bile salts from a patient comprising administering to said patient a therapeutically effective amount of a polydiallylamine polymer wherein the polydiallylamine polymer is characterized by monomeric units of the formulae:

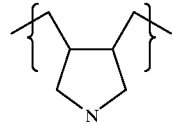

(I)

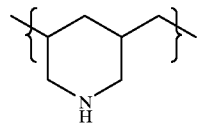

(II)

or a combination thereof and salts thereof.

11. The method of claim 10 wherein the monomeric units are in the free base form.

12. The method of claim 10 wherein the monomeric units are a salt or partial salt.

* * * * *